United States Patent [19]

Alving et al.

[11] 4,416,872

[45] Nov. 22, 1983

[54] TREATMENT OF MALARIA WITH LIPOSOMES CONTAINING 8-AMINOQUINOLINE DERIVATIVES AND GLYCOCONJUGATES

[75] Inventors: Carl R. Alving, Washington, D.C.; Edgar A. Steck, Silver Spring, Md.

[73] Assignee: The United States of America as represented by the Secretary of the Army, Washington, D.C.

[21] Appl. No.: 359,012

[22] Filed: Mar. 17, 1982

[51] Int. Cl.$^3$ ..................... A61K 37/00; C07C 103/52
[52] U.S. Cl. .............................. 424/177; 260/112.5 R
[58] Field of Search .................. 424/177; 260/112.5 R

[56] References Cited

U.S. PATENT DOCUMENTS 3,993,754  11/1976  Rahman et al. ..................... 424/177
4,224,179   9/1980  Schneider .......................... 424/177

OTHER PUBLICATIONS

Chem. Abstr., vol. 94, (1981), 132282u.
Chem. Abstr., vol. 94, (1981), 10994g.
Chem. Abstr., vol. 96, (1982), 45906y.

*Primary Examiner*—Delbert R. Phillips
*Attorney, Agent, or Firm*—William G. Gapcynski; Arthur I. Spechler; Werten F. W. Bellamy

[57] ABSTRACT

A novel treatment has been discovered for interrupting the life cycle of the malaria parasite during its development in the liver of the vertebrate host. The subject invention involves a method of chemotherapy against sporozoite-induced malaria by administering an 8-aminoquinoline drug, such as primaquine, encapsulated within liposomes containing glycoconjugates, to a vertebrate host which has been infected with sporozoites of the parasites. Preferred species of glycoconjugates have a terminal glucose or galactose moiety, such as present in glycosyl ceramide, galactosyl ceramide, lactosyl ceramide, or in glycoproteins.

64 Claims, 5 Drawing Figures

TREATMENT OF MALARIA WITH LIPOSOMES CONTAINING 8-AMINOQUINOLINE DERIVATIVES AND GLYCOCONJUGATES

The invention described herein may be manufactured and used by, or for, the Government for governmental purposes without payment of any royalty thereon.

BACKGROUND OF THE INVENTION

This invention relates to novel compositions of liposomes and their use in the effective treatment of malaria. It is well known that malaria is caused by an infection of a vertebrate host with protozoan parasites, known as Plasmodia, which are transmitted by the bite of an infected anopheline mosquito. Malaria infections in man have remained a considerable cause of morbidity and mortality despite efforts to control the mosquito vector and to eradicate infections in geographic regions roughly from 60°N to 40°S latitude. There are four species of Plasmodia that are pathogenic to man, namely: *Plasmodium falciparum; Plasmodium vivax; Plasmodium ovale;* and *Plasmodium malariae.* Each species has a developmental cycle which is initiated by the infectious forms (sporozoites) of the organism into man by the anopheline mosquito. In the human host, the sporozoites are taken up and later invade liver cells (hepatocytes) were asexual multiplication (tissue schizogony) occurs to produce organisms called merozoites. These merozoites invade red blood cells (RBC). Within the red blood cells, the parasites again undergo asexual reproduction to produce merozoites which are liberated by rupture of the host red blood cells. This process is ordinarily associated with malaria fever. These newly formed merozoites invade new red blood cells resulting in the production of gametocytes. When a blood meal is taken by the anopheline mosquito, the asexual forms of the malaria parasite are destroyed and thereafter the gametocytes undergo maturation, fertilization, and further development in the sexual cycle (sporogony) which leads to the formation of sporozoites, the infectious forms present in the salivary gland of the mosquito. In the case of *Plasmodium falciparum,* there is relatively little secondary invasion of the liver by parasites. However, secondary invasion does occur with *Plasmodium vivax* infections and, to a lesser extent, with *Plasmodium malariae* and *Plasmodium ovale* infections. Secondary invasion of the liver may give rise to multiple recurrence of malaria attacks as a consequence of development and further tissue schizogony of the parasites.

Prior to this invention, interruption of the life cycle of malaria within the host has been achieved at several stages. Measures to control the infection by eradication of mosquitos in certain areas have had a drastic effect on potential sporogony. Sporonticides (block man/vector contact) have been used with limited success to control the number of mosquitos in highly infested areas, thereby reducing the number of infectious mosquitos which are available to attack man. The interruption of schizogony in man may be achieved in tissues (tissue schizontocides) or in the blood (blood schizontocides). Additionally, sexually-differentiated forms of the malaria parasites may be attacked with gametocytocides.

Each of the foregoing means for interrupting the plasmodial life cycle has certain shortcomings. However, in the absence of superior measures, such as a vaccine, they must be relied upon at the present time.

To date, compounds which are effective against certain development stages of malaria parasites in man are known to have undersirable side effects on the host. Therefore, improvements in the treatment of malaria are being actively pursued.

Concepts on the potential applicability of liposome-targeting of drugs to malaria studies were developed based on an appreciation of the pathophysiology of malarial infection and features of its plasmodial life cycle. The parasites injected in man by the bits of the mosquito are in the form of sporozoites which travel to the liver. The organisms remain in hepatocytes for some days in the primary exoerythrocytic stage of the infection prior to emerging as exoerythrocytic schizonts and developing of a "patent" infection characterized by the appearance of parasites in erythrocytes. We have developed a novel method for "targeting" liposomes to hepatocytes.

Liposomes are defined as closed vesicles, or sacs, which contain phospholipids (examples of which are lecithin and sphingomyelin) and which may contain other lipids (examples of which are cholesterol and other sterols or steroids; charged lipids such as dicetyl phosphate and octadecylamine; glycolipids; fatty acids and other long-chain alkyl compounds; hydrophobic glycoproteins; and lipid-soluble vitamins and lipoidal surfactant-like molecules). When shaken in the presence of an excess amount of water, the lipid mixture is formed into discrete particles consisting of concentric spherical shells of lipid bilayer membranes which are referred to as multilamellar liposomes (MLL). Upon sonication, or by alternative methods of manufacture, small or large unilamellar liposomes (ULL) can be formed. In 1965, it was demonstrated that the MLL vesicle membranes were completely closed and did not allow escape of a marker compound present in the aqueous interspaces; similar properties later were found for ULL.

Numerous studies have shown that liposomes, upon injection into animals and man, are taken up rapidly by cells, and intra-cellular lysosomes, of the reticuloendothelial system, particularly those in the liver. Because of the relative impermeability of liposomes, and speedy removal of them from the circulatory system, substances (such as drugs) in the aqueous interspaces of liposomes remain concentrated and are not exposed to plasma. Moreover, there would be a strong possibility of prolonged effectiveness of a drug through slow biodegradation of the multilamellar membrane structure of the liposomes. The characteristics of liposomes thus suggest their suitability as carriers for antiparasitic agents.

SUMMARY OF THE INVENTION

The present invention relates to a novel method in the prophylaxis and chemotherapeutic treatment of malaria with newly discovered compositions comprising an antimalarial drug and a glycoconjuate encapsulated in liposomes. Liposome-containing glycoconjugates prevented patency (appearance of malaria parasites in blood) in mice previously injected with sporozoites of *Plasmodium berghei.* Glycolipids having a terminal glucose or galactose moiety, such as present in glucosyl-, galactosyl-, or lactosyl ceramide were effective when incorporated in liposomes. There were no inhibitory effects of such liposome-containing glycolipids upon development of murine malaria induced by trophozoites.

The administration of primaquine (a standard tissue-schizonticidal antimalarial drug) encapsulated in liposomes afforded little advantage over the neat drug in chemoprophylaxis of murine malaria. Some decrease in the toxicity of the primaquine resulted, yet no appreciable advantage was evident.

In the present invention, an antimalarial 8-aminoquinoline drug, such as primaquine, was incorporated within the aqueous phase of liposomes and containing the glycolipid (i.e. galactosyl ceramide) in the lipid phase. This was done in order to establish the influence of this formulation upon chemoprophylactic effects as compared to the use of the 8-aminoquinoline drug or liposomes alone. When, for example, primaquine and glycolipid were incorporated in the liposome, the potency of primaquine was enhanced very significantly in the standardized murine test system in which sporozoites of P. berghei were injected.

DETAILED DESCRIPTION OF THE INVENTION

The specific embodiments of this invention relate to novel compositions and method for treating sporozoite-induced malaria through parenteral administration of glycoconjugates and 8-aminoquinolines, such as primaquine incorporated in liposomes, and use thereof as a highly effective chemoprophylactic antimalarial agent.

Surprisingly, the foregoing development represents a new and highly effective treatment for malaria with a novel composition which interrupts the life cycle of malaria parasites within the liver of the host animal. This newly discovered chemotherapeutic treatment of malaria represents a major advance in medicinal chemistry. The significance of our finding takes on added humanitarian dimensions when it is realized that malaria is the prime infections disease of man, and is responsible for more than one million deaths annually among the world population. The painful and progressive development of this disease is initiated by the injection of sporozoites from malaria parasites into a mammal by an infected anopheline mosquito. The infectious parasites travel to the liver of the host. Once in the liver cells, the sporozoites undergo transformations in hepatocytes to the exoerythrocytic stage of Plasmodia within several days. Shortly thereafter, the newly formed exoerythrocytic schizonts begin to invade circulating red blood cells. The appearance of malaria parasites in the red blood cells of the blood is referred to as the patent development stage of the malaria infection. The stage of development of the disease from injection of parasites and prior to its appearance in the red blood cells is called the pre-patent period.

In the present invention, a novel treatment has been developed which results in a lethal intrusion upon the life cycle of the malaria parasite during the pre-patent period. This treatment prevents Plasmodia from appearing in the red blood cells, and hence, the patent malaria infection does not occur. In highly standardized testing, liposomes containing neutral glycolipids (bearing a terminal glucose or galactose moiety) were shown to prevent patent malarial infections in some animals previously injected with highly infectious malaria sporozoites. The effects were especially significant against the parasites at stages in the pre-patent period. However, the encapsulated glycolipids per se failed to prevent infections resulting from injection of blood containing red blood cell forms (trophozoites) of the malaria parasites. It was established that the carbohydrate moiety was necessary as part of the glycolipids. We observed that both phosphocholine ceramide (sphingomyelin) and ceramide alone, incorporated in liposomes, failed to inhibit patent development of Plasmodia berghei infections. It was further discovered that the negatively-charged compounds 3-sulfogalactosyl ceramide (sulfatide) and galactose-N-acetyl-galactosamine-galactose(N-acetyl-neumaminic acid) glucose-ceramide (ganglioside $G_{M1}$) in liposomes were ineffective in preventing patency. Apparently, the liposomal glycolipids block the interactions of malaria parasites with cellular membranes during the intra-hepatic phase of the infection. Liposomes themselves afforded some useful interference with the life cycle of the parasite during the pre-patent period. It appears that the liposomes containing the effective glycolipids may be recognized by, and then internalized by, mammalian cells in this novel means for inteference with the life cycle of malaria parasites.

Primaquine has long been used with success against hepatic forms of malaria parasites, although toxic effects are frequently evident. Hence, there is an urgent need for a more effective treatment. Accordingly, we decided to investigate and evaluate the effectiveness of (1) primaquine incorporated in liposomes and (2) primaquine and galactosyl ceramide, incorporated in liposomes. We observed that although primaquine encapsulated into liposomes was less toxic than the neat drug, no appreciable improvement in therapeutic effect resulted. Further, we observed that the use of the glycolipid per se in liposomes prevented patency in some test animals. However, the combination of primaquine and galactosyl ceramide provided an unexpectedly superior improvement in the effective treatment of hepatic forms of malaria parasites. This finding underscores the novel and significant medical advance achieved by the present invention.

In sum, the present invention relates to the effective treatment of malaria with antimalarial compositions comprising either a glycolipid alone, a glycoprotein encapsulated within a liposome, or an 8-aminoquinoline drug and a glycoconjugate contained within a liposome. The 8-aminoquinoline component is preferably represented by primaquine. The liposome (exclusive of the glycoconjugate constituent) may contain a combination of (1) a phospholipid and cholesterol or (2) a phospholipid, cholesterol and a negatively or positively charged (lipophilic) amphipathic compound. The phospholipid component may be selected from the group comprising any lipid capable of forming liposomes, including, but not limited to: any phosphatidyl-choline derivative, glycerophosphatides, lysophosphatides, spingomyelins, and mixtures thereof. The negatively charged (lipophilic) amphipathic compounds may be selected from the group comprising di(alkyl)phosphates, phosphatidic acid, phosphatidylserine, phosphatidylglycerol, phosphatidylinositol, dicetyl phosphate, or an other similar negatively charged amphipathic compound that can impart a negative charge to a liposome surface. When positively charged (lipophilic) amphipathic compounds are employed; they are selected from the group comprising alkyl amines, such as stearylamine and hexadecylamine. The glycoconjugate component may be selected from compounds such as a ceramide containing a glucose, galactose, or a lactose moiety, or other glycolipids having these carbohydrates. The liposomal glycoconjugate may also include a glycoprotein, including, but not limited to, asialoorosomucoid, orosomucoid, asialofetuin, or fetuin.

EXAMPLES

Examples herein offered to illustrate the invention are not intended to limit the scope thereof regarding therapeutic effects of glycoconjugates, in liposomes, or the combination of primaquine encapsulated in liposomes containing glycoconjugates, upon sporozoite-induced malaria. For convenience, liposomes have been made with beta,gamma-dimyristoyl phosphatidyl choline (DMPC), or with beta,gamma-dipalmitoylphosphatidylcholine (DPPC), or with beta,gamma-distearoyl phosphatidylcholine (DSPC) as the phospholipid component. Cholesterol (Ch) was selected as the steroidal component of the liposomes. To impart charge to the liposomes, the amphiphilic component was conveniently chosen as either dicetyl phosphate (DCP) or stearylamine (SA).

All temperatures are given as degrees Celsius (°C.), and parts or percentages are on the weight basis.

Materials

For convenience in preparation of liposomes, stock solutions in chloroform were prepared for the phospholipids, cholesterol, and the amphiphilic component, and those were all stored at $-20°$. A commercial normal saline solution was used as the 0.154 M sodium chloride. All phospholipids, amphiphilic components, glycolipids, and primaquine diphosphate were commercial products.

Methods

Liposomes

Liposomes were prepared by standard procedures. The molar ratios of dimyristoyl (or dipalmitoyl) phosphatidylcholine (DMPC or DPPC), cholesterol (Ch), and dicetyl phosphate (DCP) were 1:0.75:0.11 in all instances except when sphingomyelin was added. To that basic composition, 100 micrograms of ceramide lipid was added per micromole of phosphatidyl choline. Upon use of spingomyelin (phosphocholine ceramide), the molar ratios of phosphatidylcholine, sphingomyelin, cholesterol, and dicetyl phosphate were 0.8:0.2:0.75:0.11, respectively. The phosphatidylcholine, or phosphatidylcholine plus sphingomyelin, was 10 mM with respect to the sodium chloride (0.15 M) or primaquine (0.146 M) solution used for swelling the liposomes. The primaquine diphosphate was in the form of a 0.146 M solution as employed in swelling the liposomes, and its amount was based upon desired dose levels to be administered to the animals in liposomes. The liposomes were separated, diluted with some volumes of 0.154 M NaCl solution for washing, then spun down at ca. 27,000 g at 20° for 10 minutes. The supernatant was discarded, and the liposome pellet was suspended in 0.154 M NaCl (ca. one-quarter of the volume used in swelling of the liposomes) and that administered to the mice by intravenous injection. Amounts given were usually 0.15 ml to 0.2 ml range. When glycoproteins were utilized, fetuin or asialofetuin was present in the swelling solution in the concentration of 10 mg per ml of 0.15 M sodium chloride. The liposomes formed in the presence of glycoproteins were not washed free of unencapsulated protein.

Animal Studies (a) Sporozoite-Induced Infections

The mass isolation of salivary glands from *Anopheles stephensi* was done with *Plasmodium berghei* (NK 65 or ANKA strain), using the method of Bosworth, et al [J. Parasitol., 61, 769–772 (1975)]. The mosquitoes (India strain) were fed on infected mice and maintained at 21° and a relative humidity of 80 percent to ensure optimum development of the parasite. It was most satisfactory to isolate the salivary glands some 18 to 25 days after the mosquitoes had taken their infectious blood meal. Sporozoites were liberated by triturating the glands in a glass syringe, and counted in a haemocytometer. The sporozoites were suspended in Medium 199 for a concentration of 1 to $2 \times 10^5$ per ml. Mice were injected by intravenously injecting 0.1 to 0.2 ml of the suspension of sporozoites. Appearance of parasites in the blood (patency) occurred in $(5.1 \pm 1)$ days in unmedicated animals. After injection of $3 \times 10^4$ sporozoites, a mouse showed 0.79 parasites per $10^{10}$ RBC in one week. In experiments with liposomes, mice were used one day following injection of sporozoites.

(b) Trophozoite-Induced Infection.

The infection of mice with *P. berghei* trophozoites in the blood of donor mice was done after the method of Osdene, et al [J. Med. Chem., 10, 431–434 (1967)].

EXAMPLE 1

Primaquine Encapsulated in Negative Liposomes

Primaquine diphosphate solution was used for swelling DDPC/Ch/DCP mixture into liposomes, and the resulting liposomes were washed by centrifugation, and then suspended in a volume of saline four times of that used in swelling the vesicles. The concentration of drug was equivalent to 25 mg/kg primaquine diphosphate for 35 g mice when 0.1 ml was injected, or 376 mg/kg for 0.15 ml, or 50 mg/kg for 0.2 ml.

Controls received liposomes swollen in saline at the 0.2 ml level. The liposome preparations were injected intravenously into mice which had been infected with *P. berghei* sporozoites one day previously.

Figure 1:
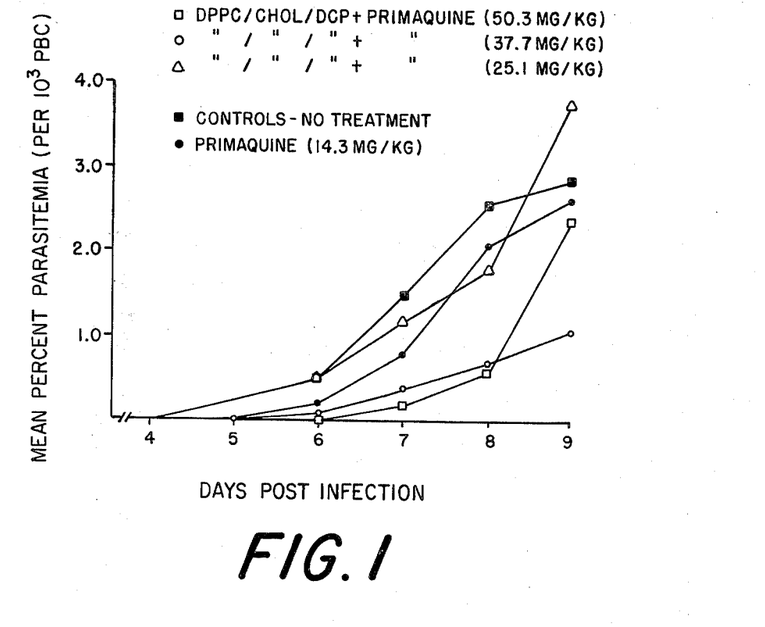

Control mice all developed patent *P. berghei* infections: on day four post-infection, one of eight animals had parasitemia; on day five, 6/8; on day six, ⅞; on day eight, 8/8. Of mice given primaquine diphosphate in saline at a dose of 14 mg/kg, 87.5 percent (⅞) showed parasitemia by day six (day four, ⅛; day five, 4/8; day six, ⅞). In those mice given primaquine in liposomes by intravenous route, there were some deaths at injection: at 25 mg/kg, 1/6; at 37.6 mg/kg, ⅛; at 50 mg/kg, ⅜. Among those in the first group, 4/5 showed parasitemia by day six; the second group, 6/7 by day nine (4/7 or day six), and the third group, 3/3 on day 7. In FIG. 1 there are depicted results from the several trials with primaquine incorporated in liposomes. It is apparent that an extremely slight, if any, therapeutic advantage has been gained by having the drug encapsulated in liposomes. Here, the effect of liposome-encapsulated primaquine on *Plasmodium berghei* infection in mice is illustrated. The liposomes (lacking a glycoconjugate) were injected one day following infection by sporozoites. Each point is an average of values determined in three to eight mice.

EXAMPLES 2-8

Glycolipids, and Other Lipids, Incorporated in Negative Liposomes

Table I shows the effects of alterations of the sugar moieties among various ceramide lipids which were incorporated in DMPC/Ch/DCP liposomes. In those cases, the control animals received no medication after infection with *P. berghei* sporozoites, only saline being given. Examples 2, 3 and 4 show that neutral glycolipids bearing a carbohydrate function are needed to inhibit patency, as evident from comparison with Examples 5, 6, 7 and 8.

Figure 2:
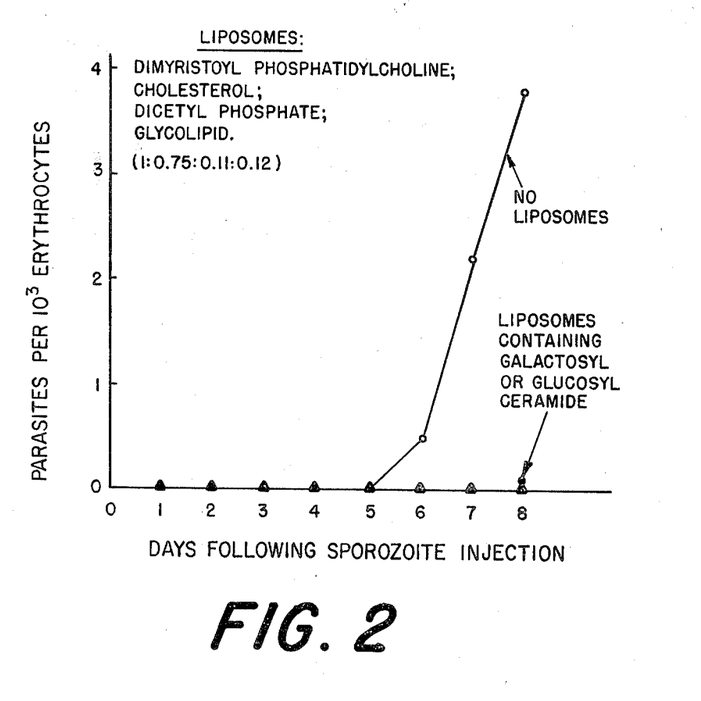

Further attention was given to probing effectiveness of galactosyl ceramide and of glucosyl ceramide in liposomes for treatment of *P. berghei* infection, as monitored by appearance of parasites in RBC of mice injected with sporozoites of the organism. In these experiments, the infection was considered patent even if only one parasite was detected among $10^5$ erythrocytes. The results are illustrated in FIG. 2. Here, the inhibition of erythrocytes parasites after injection of liposomes containing glycolipids is depicted. The animals were injected intravenously with liposomes one day after sporozoite injection. Each point represents the mean of 10 to 11 animals.

TABLE I

INFLUENCE OF SACCHARIDE ATTACHMENT ON INHIBITORY EFFECTS OF CERAMIDE LIPIDS IN LIPOSOMES

| Example | Ceramide Lipid | Number of Animals* With Patent Infections | Number of Animals* Injection | Patency (%) | Average Pre-Patent Period (days)+ |
|---|---|---|---|---|---|
| 1 | Control (no Liposomes) | 49 | 62 | 79 | 5.1 ± 1 |
| 2 | Glucosylceramide | 2 | 28 | 7.4 | 6.0 |
| 3 | Galactosyceramide | 6 | 40 | 15 | 7.3 ± 1.6 |
| 4 | Lactosylceramide | 1 | 7 | 14 | 6.0 |
| 5 | Ceramide | 6 | 7 | 86 | 6.3 ± 0.8 |
| 6 | Phosphocholine Ceramide (Sphingomyelin) | 5 | 7 | 71 | 6.2 ± 0.4 |
| 7 | Sulfogalactosyl Ceramide (Sulfatide) | 5 | 7 | 71 | 5.8 ± 0.8 |
| 8 | Ganglioside $G_{M1}$ | 5 | 7 | 71 | 6.4 ± 0.9 |

*Animals were examined for patency daily during three to eight days after injection of sporozoites. Patency was defined as at least one parasite per $10^5$ erythrocytes.
+Values given as mean ± standard deviation.

EXAMPLE 9

Variation of Phospholipids in Liposomes Containing Galactosyl Ceramide

The phospholipid component (PL) was varied in liposomes formulated as PC/Ch/DCP with galactosyl ceramide. Selected as PL were: dimyristoyl phosphatidylcholine (DMPC); dipalmitoyl phosphatidylcholine (DPPC); distearoyl phosphatidylcholine (DSPC); and sphingomyelin (SM). All liposomes were swollen in normal saline, and controls were injected with saline solution, only.

Six of eight control mice had developed patent *P. berghei* infections by day eight following injection of sporozoites, whereas none of the eight mice in each of the other groups gave evidence of blood infection by day ten after sporozoites had been given.

EXAMPLE 10

Variation in Amphipathic Compounds in Liposomes Containing Glycolipids or Other Lipids The character of charge on liposomes containing galactosyl ceramide was altered, using compositions: DPPC/Ch/DCP; DPPC/Ch/SA; DPPC/Ch, only; and DPPC and DCP without cholesterol. All lipid films were swollen in normal saline and NaCl solution was used as control.

Three of seven control mice developed patent infections by day six following injection of sporozoites. DPPC/Ch/DCP trials showed patency in one of eight mice on day seven; DPPC/Ch/SA, one of seven on day seven; DPPC/Ch, none of seven had patent infections on day ten; and DPPC/DCP, one of eight were patent on day seven.

Another series of trials was done with: DPPC/Ch/DCP; DPPC/Ch/SA; DPPC/Ch; DPPC/DCP; DPPC/SA; and DPPC alone, all containing glucosyl ceramide. The lipid mixtures were swollen in normal saline, controls were given NaCl only.

All eight control mice had developed patent infections by day 11. In the DPPC/Ch/DCP group, one of eight mice developed blood infection (day six). DPPC/Ch/SA animals (eight) showed one patent infection at day eight; DPPC/Ch, of eight at day eight; DPPC/DCP, one of eight at day seven; DPPC/SA, three of eight at day six; and DPPC, only, three of eight animals at day seven.

EXAMPLE 11

Therapeutic Effect of Liposomes Containing Galactosyl Ceramide

Figure 3:
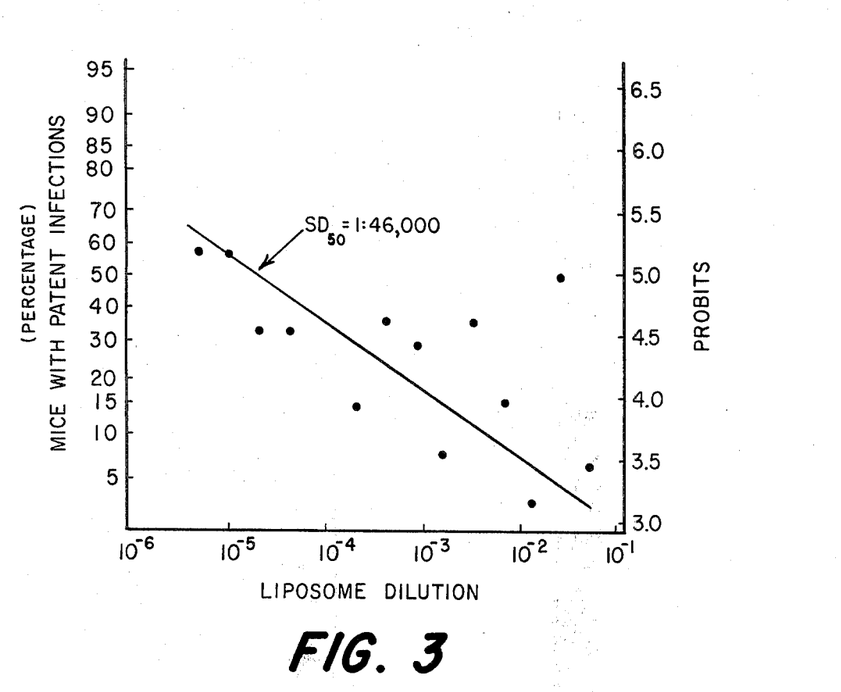

DPPC/Ch/DCP liposomes containing 0.123 micromoles of galactosyl ceramide per micromole of DPPC were prepared by swelling in normal saline in the usual way. The liposomes were diluted from 1:20 to 1:204,800 using normal saline. The results are shown in Table II. Seven to ten mice were used for each treatment group. The number of patent infections observed after 10-16 days was tabulated and compared with a control group of animals that received intravenous infusions of normal saline solution instead of liposomes. Not all of the control animals developed a patent infection; a fraction of susceptibles became patent after injection of normal saline. The ratio of these fractions times 100 represented the adjusted percentage, based on susceptible animals, that became patent following treatment with liposomes. For example, if 6/8 (0.75) of control animals, and 2/8 (0.25) of liposome treatment animals became patent, the adjusted percentage of patency among liposome treated animals would be 0.25/0.75×100=33 percent. Results calculated in this way are shown in Table II, and illustrated in FIG. 3. The data in FIG. 3 were plotted using a probit scale (on right), which converts a sigmoid curve to a straight line. The corresponding percentage of mice with patent infections is shown on a parallel scale concept. The dilution of liposomes that resulted in 50 percent of the mice having patent infections (i.e., where the efficacy of the treatment diminished by 50 percent, also called $SD_{50}$) was 1:46,000. Here, the therapeutic effect of liposomes containing galactosyl ceramide is illustrated. Each point represents data derived from seven to 26 animals. The percentage of animals that became patent was corrected by comparing with control animals injected only with saline. Of 209 control mice, 155 (74.2 percent) became patent, and this value (0.742) was considered and the "100 percent" value for the therapeutic group.

TABLE II

THERAPEUTIC EFFECT OF GALACTOSYL CERAMIDE-CONTAINING LIPOSOMES SWOLLEN IN SALINE

| Experiment No. | Liposome Dilution | Number Patent Total Number | % Patent Compared to Controls Individual Expt. | Average |
|---|---|---|---|---|
| 17 | 1:20 | 1/8 | 12.5 | |
| 19 | | 0/7 | 0 | 6.3 |
| 19 | 1:40 | 2/7 | 50 | 50 |
| 19 | 1:80 | 0/7 | 0 | |
| 21 | | 1/10 | 10 | |
| 47 | | 0/8 | 0 | 3.3 |
| 19 | 1:160 | 0/7 | 0 | 15 |
| 21 | | 3/10 | 30 | |
| 19 | 1:320 | 2/7 | 50 | |
| 21 | | 3/10 | 30 | 35.1 |
| 23 | | 2/9 | 25.4 | |
| 23 | 1:640 | 1/8 | 14.3 | 7.2 |
| 29 | | 0/10 | 0 | |
| 23 | 1:1,280 | 2/8 | 28.6 | 28.6 |
| 23 | 1:2,560 | 4/8 | 57.1 | |
| 29 | | 1/8 | 14.1 | 35.6 |
| 23 | 1:5,120 | 1/8 | 14.3 | 14.3 |
| 31 | 1:25,600 | 2/8 | 32.1 | 32.1 |
| 31 | 1:51,200 | 2/8 | 32.1 | 32.1 |
| 33 | 1:102,400 | 4/9 | 47.1 | 57.1 |
| 33 | 1:204,800 | 4/9 | 57.1 | 57.1 |

EXAMPLE 12

Therapeutic Effect of Liposomes Containing Galactosyl Ceramide and Primaquine

Liposomes (as in Example 11) were prepared from DPPC/Ch/DCP and galactosyl ceramide by swelling in primaquine diphosphate solution. Thereafter, the liposomes were diluted in normal saline as described in Example 11. Saline controls were used, and calculations were performed, also as described in Example 11. The results are shown in Table III and illustrated in FIG. 4. Here, the therapeutic effect of liposomes containing galactosyl ceramide having encapsulated primaquine is depicted. Each point represents data derived from 8 to 24 animals. The percent of animals that became patent was corrected by comparing with control animals injected only with saline. Of 209 control mice, 155 (74.2 percent) became patent, and this value (0.742) was considered as the "100 percent" value for the therapeutic group.

TABLE III

THERAPEUTIC EFFECT OF GALACTOSYL CERAMIDE-CONTAINING LIPOSOMES SWOLLEN IN PRIMAQUINE

| Experiment No. | Liposome Dilution | Number Patent Total Number | % Patent Compared to Controls Individual Expt. | Average |
|---|---|---|---|---|
| 46 | 1:80 | 0/8 | 0 | 0 |
| 29 | 1:1,280 | 1/8 | 14.1 | |
| 43 | | 3/8 | 60 | |
| 45 | | 0/8 | 0 | 24.7 |
| 29 | 1:2,560 | 0/8 | 0 | |
| 40 | | 3/8 | 75 | 37.5 |
| 47 | 1:5,120 | 0/8 | 0 | 0 |
| 31 | 1:25,600 | 2/8 | 25 | |
| 43 | | 1/8 | 12.5 | |
| 45 | | 2/8 | 25 | 20.8 |
| 31 | 1:51,200 | 0/8 | 0 | |
| 40 | | 3/8 | 75 | 37.5 |
| 33 | 1:204,800 | 3/9 | 42.8 | 42.8 |
| 43 | 1:512,000 | 8/8 | 100 | |

TABLE III-continued

THERAPEUTIC EFFECT OF GALACTOSYL CERAMIDE-CONTAINING LIPOSOMES SWOLLEN IN PRIMAQUINE

| Experiment No. | Liposome Dilution | Number Patent Total Number | % Patent Compared to Controls Individual Expt. | Average |
|---|---|---|---|---|
| 47 | | 2/8 | 55 | 77.5 |
| 40 | 1:1,024,000 | 5/8 | 100 | |
| 45 | | 4/8 | 80 | 90 |
| 40 | 1:1,536,000 | 4/8 | 100 | |
| 47 | | 4/8 | 100 | 100 |

Figure 4:
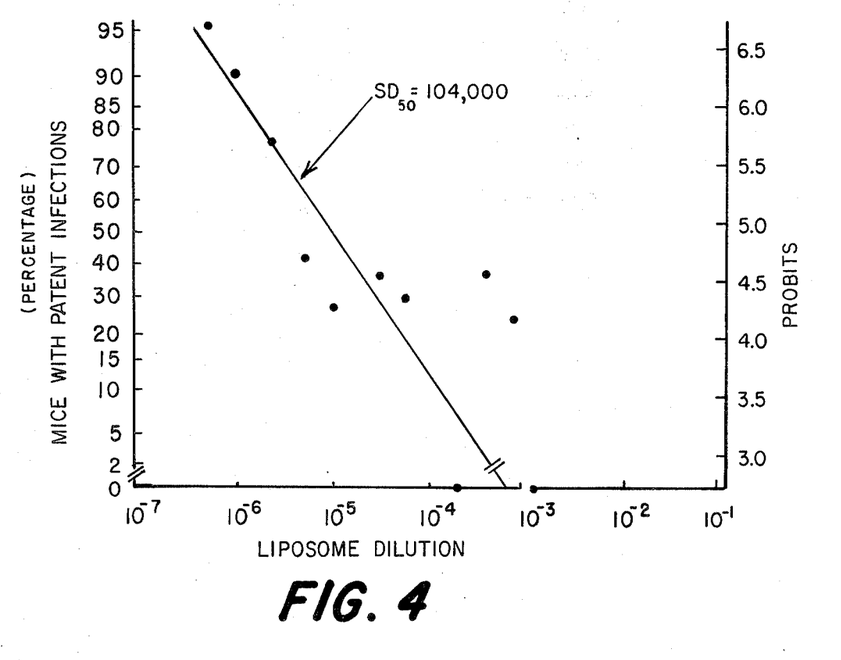

The data in FIG. 4 were plotted using a probit scale, as in Example 11. The dilution of liposomes containing primaquine that resulted in 50 percent of the mice having patent infections was 1:104,000. Thus, liposomes containing primaquine and galactosyl ceramide had approximately 126 percent greater efficacy than did liposomes containing only galactosyl ceramide [(104,000−46,000)/46,000×100/1=58.7 percent]. Stated from another perspective, primaquine encapsulated within liposomes containing galactosyl ceramide was more than 46,000 times more effective than primaquine not encapsulated within liposomes containing galactosyl ceramide. This is based on the fact that a 1:46,000 dilution of primaquine alone would not be expected to have any detectable efficacious effect (see, for example, dilutions of primaquine shown in FIG. 1).

EXAMPLE 13

Therapeutic Effects of a Glycolipid Alone (in the Absence of Liposomes) on Sporozoite-Induced *P. berghei* Infections In other examples, glycolipids, such as galactosyl ceramide, were included as constituents of liposomes that contained a phospholipid as the major component. As shown in Table IV, galactosyl ceramide by itself, in the absence of liposomes containing a phospholipid, also had substantial efficacious effects.

EXAMPLE 14

Lack of Effects of Glycoproteins Alone, in the Absence of Lipsomes, on Sporozoite-Induced *P. berghei* Infections When fetuin, orosomucoid, asialofetuin or asialoorosomucoid were tested for antimalarial properties in sporozoite-induced malaria, they completely lacked efficacy (Table V).

EXAMPLE 15

Therapeutic Effects of Liposome-Associated Glycoproteins

When fetuin, orosomucoid, asialofetuin or asialoorosomucoid were incorporated as constituents in the liposomal membranes during the liposome formulation, the resulting liposome-glycoprotein combinations had striking therapeutic activities against sporozoite-induced malaria (Table VI). When different doses of liposome-glycoprotein complex were tested, even a fifty-fold or a hundred-fold dilution still retained virtually maximal activity (Table VI).

TABLE IV

THERAPEUTIC EFFECTS OF GLYCOLIPIDS ALONE IN THE ABSENCE OF LIPOSOMES CONTAINING PHOSPHOLIPIDS

| Experiment No. | Amount of Galactosylceramide Injected (Pico-moles) | Number Patent Total Number | % Patent Compared to Controls |
|---|---|---|---|
| 68 | 1845 | 0/7 | 0 |
| 69 | 184.5 | 2/8 | 35 |
| 69 | 18.45 | 4/5 | 70 |

TABLE 5

LACK OF EFFECTS OF GLYCOPROTEINS ALONE

| Experiment No. | Substance Injected | Amount Injected (mg) | Number Patent Total Number | % Patent |
|---|---|---|---|---|
| 70, 71, 73 | Normal Saline | | 19/31 | 61 |
| 70, 71, 73 | Asialo Orosomucoid | 1.5 | 14/28 | 50 |
| 73 | Asialo Fetuin | 1.5 | 4/10 | 40 |

TABLE VI

THERAPEUTIC EFFECTS OF LIPOSOME-ASSOCIATED GLYCOPROTEINS

| Experiment No. | Substance Injected | Amount Injected (mg) | Number Patent Total Number | % Patent |
|---|---|---|---|---|
| 74, 75, 82, 87, 90, 91 | Normal Saline | | 37/60 | 68 |
| 74 | Liposomes Containing Asialofetuin | 1.5 | 0/7 | 0 |
| 75, 82 | Liposomes Containing Asialofetuin | 0.15 | 2/16 | 12.5 |
| 90 | Liposomes Containing Asialofetuin | 0.075 | 1/10 | 10 |
| 91 | Liposomes Containing Asialofetuin | 0.015 | 4/10 | 40 |
| 74 | Liposomes Containing Fetuin | 1.5 | 3/9 | 33 |
| 75, 82, 87 | Liposomes Containing Fetuin | 0.15 | 9/24 | 37.5 |
| 90 | Liposomes Containing Fetuin | 0.075 | 2/10 | 20 |
| 91 | Liposomes Containing Fetuin | 0.015 | 1/10 | 10 |

All ten of ten controls had patent infections six days after injections of sporozoites. In the case of glucosyl ceramide, liposomes given seven days prior to infection showed that seven of nine mice were patent on day six after infection; the five-day group had seven of ten animals patent on day seven post-infection; and those treated one day before infection had seven of nine patent on day six after infections. With the DPPC/Ch/DCP liposomes lacking the neutral glycolipid, eight of nine mice treated seven days prior to infection showed patency on day six post-infection; all ten injected with liposomes five days prior to the sporozoites had patent infections by day ten; six of ten mice injected on day before the sporozoites showed blood infectioned by day nine.

EXAMPLE 16

Effects of Galactosyl Ceramide Liposomes on Trophozoite-Induced *P. berghei* Infections.

Figure 5:
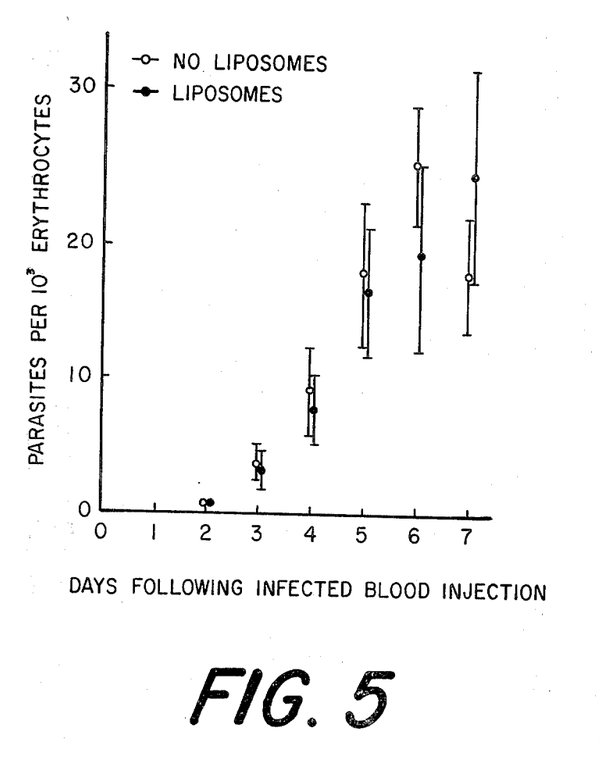

Examples 1–12 have established that liposome-encapsulated neutral glycolipids interfere with pre-erythrocytic development of *P. berghei* introduced in the form of sporozoites. This specific fact was evident in that galactosyl ceramide in liposomes did not inhibit parasitemia in mice infected with *P. berghei* trophozoites (blood-induced infection). FIG. 5 shows graphically the results of experiments in which mice were infected with trophozoites and treated on day post-infection. It is shown that response to galactosyl ceramide was little different in effects from those shown in saline controls. Hence, the absence of liposomal-inhibition of erythrocytic parasites in animals injected with infected blood is depicted. Liposomes containing galactosyl ceramide were administered to 14 mice one day after injection of infected blood. The control group consisted of 12 mice that received saline instead of liposomes. Each point represents the mean±standard deviation. The infected blood (0.1 ml) was drawn from a mouse with a patent infection one week after it had been injected with $3 \times 10^4$ sporozoites; the blood contained 0.19 parasite per $10^3$ erythrocytes.

We claim:

1. A An antimalarial composition comprising a glycoconjugate selected from the group consisting of:
   (a) a glycolipid having a terminal carbohydrate moiety selected from the group consisting of glucosyl, galactosyl and lactosyl;
   (b) a glycolipid having a terminal carbohydrate moiety selected from the group consisting of glucosyl, galactosyl and lactosyl encapsulated within a liposome selected from the group consisting of a phospholipid and cholesterol-containing liposome, and a phospholipid, cholesterol and a charged (lipophilic) amphipathic compound-containing liposome;
   (c) a glycoprotein selected from the group consisting of fetuin, asialofetuin, orosomucoid and asialoorosomucoid encapsulated within a liposome selected from the group consisting of phospholipid and cholesterol-containing liposome, and a phospholipid, cholesterol and a charged (lipophilic) amphipathic compound-containing liposome;
   (d) a glycolipid having a terminal carbohydrate moiety selected from the group consisting of glucosyl, galactosyl and lactosyl encapsulated within a liposome selected from the group consisting of a phospholipid and cholesterol-containing liposome, and a phospholipid, cholesterol and a charged (lipophilic) amphipathic compound-containing liposome wherein each said liposome contains an 8-aminoquinoline selected from the group consisting of primaquine and a pharmaceutically-acceptable acid addition salt thereof; and
   (e) a glycoprotein selected from the group consisting of fetuin, asialofetuin, orosomucoid and asialoorosomucoid encapsulated within a liposome selected from the group consisting of a phospholipid and cholesterol-containing liposome, and a phospholipid, cholesterol and a charged (lipophilic) amphipathic compound-containing liposome wherein each said liposome contains an 8-aminoquinoline selected from the group consisting of primaquine and a pharmaceutically-acceptable acid addition salt thereof.

2. The composition of claim 1 wherein the glycoconjugate is selected from the group consisting of:
   (a) a glycolipid having a terminal carbohydrate moiety selected from the group consisting of glucosyl, galactosyl and lactosyl;
   (b) a glycolipid having a terminal carbohydrate moiety selected from the group consisting of glucosyl, galactosyl and lactosyl encapsulated within a liposome selected from the group consisting of phospholipid and cholesterol-containing liposome, and a phospholipid, cholesterol and a charged (lipophilic) amphipatic compound-containing liposome; and (c) a glycolipid having a terminal carbohydrate moiety selected from the group consisting of glucosyl, galactosyl and lactosyl encapsulated within a liposome selected from the group consisting of a phospholipid and cholesterol-containing liposome, and a phospholipid, cholesterol and a charged (lipophilic) amphipathic compound-containing liposome wherein each said liposome contains an 8-aminoquinoline selected from the group consisting of primaquine and a pharmaceutically-acceptable acid addition salt thereof.

3. The composition of claim 2 wherein the glycoconjugate is a glycolipid having a terminal carbohydrate moiety selected from the group consisting of glycosyl, galactosyl and lactosyl.

4. The composition of claim 2 wherein the glycoconjugate is a glycolipid having a terminal carbohydrate moiety selected from the group consisting of glycosyl, galactosyl and lactosyl encapsulated within a liposome selected from the group consisting of phospholipid and cholesterol-containing liposome, and a phospholipid, cholesterol and a charged (lipophilic) amphipathic compound-containing liposome.

5. The composition of claim 2 wherein the glycoconjugate is a glycolipid which contains a terminal carbohydrate moiety selected from the group consisting of glucosyl, galactosyl and lactosyl encapsulated within a lipsome selected from the group consisting of a phospholipid and cholesterol-containing liposome, and a phospholipid, cholesterol and a charged (lipophilic) amphipathic compound-containing liposome wherein each said liposome contains an 8-aminoquinoline selected from the group consisting of primaquine and a pharmaceutically-acceptable acid addition salt thereof.

6. The composition of claim 3 wherein the glycolipid is ceramide.

7. The composition of claim 4 wherein the glycolipid is ceramide.

8. The composition of claim 5 wherein the glycolipid is ceramide.

9. The composition of claim 6 wherein the carbohydrate moiety is glucosyl.

10. The composition of claim 6 wherein the carbohydrate moiety is galactosyl.

11. The composition of claim 6 wherein the carbohydrate moiety is lactosyl.

12. The composition of claim 7 wherein the carbohydrate moiety is glucosyl.

13. The composition of claim 7 wherein the carbohydrate is galactosyl.

14. The composition of claim 7 wherein the carbohydrate is lactosyl.

15. The composition of claim 8 wherein the carbohydrate is glycosyl.

16. The composition of claim 8 wherein the carbohydrate is galactosyl.

17. The composition of claim 8 wherein the carbohydrate is lactosyl.

18. The composition of claim 16 wherein the liposome contains a phospholipid, cholesterol and a charged (lipophilic) amphipathic compound.

19. The composition of claim 18 wherein the phospholipid is beta, gamma-dipalmitoylphosphatidylcholine and the charged (lipophilic) amphipathic compound is diacetyl phosphate.

20. The composition of claim 19 wherein the 8-aminoquinoline is primaquine diphosphate.

21. The composition of claim 1 wherein the glycoconjugate is selected from the group consisting of:

(a) a glycoprotein selected from the group consisting of fetuin, asialofetuin, orosomucoid and asialoorosomucoid encapsulated within a lipsome selected from the group consisting of a phospholipid and cholesterol-containing liposome, and a phospholipid, cholesterol and a charged (lipophilic) amphipathic compound-containing liposome; and (b) a glycoprotein selected from the group consisting of a phospholipid and cholesterol-containing liposome, and a phospholipid, cholesterol and a charged (lipophilic) amphipathic compound-containing liposome wherein each said liposome contains an 8-aminoquinoline selected from the group consisting of primaquine and a pharmaceutically-acceptable acid addition salt thereof.

22. The composition of claim 21 wherein the glycoconjugate is a glycoprotein selected from the group consisting of fetuin, asialofetuin, orosomucoid and asialoorosomucoid encapsulated within a liposome selected from the group consisting of a phospholipid and cholesterol-containing liposome, and a phospholipid, cholesterol and a charged (lipophilic) amphipathic compound-containing liposome.

23. The composition of claim 21 wherein the glycoconjugate is a glycoprotein selected from the group consisting of fetuin, asialofetuin, orosomucoid and asialoorosomucoid encapsulated within a liposome selected from the group consisting of a phospholipid and cholesterol-containing liposome, and a phospholipid, cholesterol and a charged (lipophilic) amphipathic compound-containing liposome wherein each said liposome containins an 8-aminoquinoline selected from the group consisting of primaquine and a pharmaceutically-acceptable acid addition salt thereof.

24. The composition of claim 1 wherein the liposome is selected from the group consisting of a phospholipid and cholesterol-containing liposome, and a phospholipid, cholesterol and a charged (lipophilic) amphipathic compound-containing liposome.

25. The composition of claim 24 wherein the liposome contains a phospholipid and cholesterol.

26. The composition of claim 24 wherein the liposome contains a phospholipid, cholesterol and the additional charged lipid is a (lipophilic) amphipathic compound.

27. The composition of claim 25 wherein the phospholipid is selected from the group consisting of a phosphatidylcholine derivative, glycerophosphatide, a lysophosphatide, spingomyelin and mixtures thereof.

28. The composition of claim 26 wherein the phospholipid is selected from the group consisting of a phosphatidyl choline derivative, glycerophosphatide, a lysophosphatide, spingomyelin and mixtures thereof.

29. The composition of claim 26 wherein the charged amphipathic lipid compound is negatively charged.

30. The composition of claim 26 wherein the charged amphipathic lipid compound is positively charged.

31. The composition of claim 29 wherein the charged amphipathic lipid compound is selected from the group comprising a di(alkyl) phosphate, a phospholipid, phosphatidic acid, phosphatidylserine, and phosphatidylinositoyl.

32. The composition of claim 30 wherein the charged amphipathic lipid compound is selected from the group comprising long-chain alkylamines, stearylamine, and hexadecylamine.

33. A method for treating malaria which comprises the step of administering to an infected animal a therapeutically effective amount of an antimalarial composition comprising a glycoconjugate selected from the group consisting of:
(a) a glycolipid having a terminal carbohydrate moiety selected from the group consisting of glucosyl, galactosyl and lactosyl;
(b) a glycolipid having a terminal carbohydrate moiety selected from the group consisting of gucosyl, galactosyl and lactosyl encapsulated within a liposome selected from the group consisting of a phospholipid and cholesterol-containing liposome, and a phospholipid, cholesterol and a charged (lipophilic) amphipathic compound-containing liposome;
(c) a glycoprotein selected from the group consisting of fetuin, asialofetuin, orosomucoid and asialoorosomucoid encapsulated within a liposome selected from the group consisting of phospholipid and cholesterol-containing liposome, and a phospholipid, cholesterol and a charged (lipophilic) amphipathic compound-containing liposome;
(d) a glycolipid having a terminal carbohydrate moiety selected from the group consisting of glycosyl, galactosyl and lactosyl encapsulated within a liposome selected from the group consisting of a phospholipid and cholesterol-containing liposome, and a phospholipid, cholesterol and a charged (lipophilic) amphipathic compound-containing liposome wherein each said liposome contains an 8-aminoquinoline selected from the group consisting of primaquine and a pharmaceutically-acceptable acid addition salt thereof; and
(e) a glycoprotein selected from the group consisting of fetuin, asialofetuin, orosomucoid and asialoorosomucoid encapsulated within a liposome selected from the group consisting of a phospholip and cholesterol-containing liposome, and a phospholipid, cholesterol and a charged (lipophilic) amphipathic compound-containing liposome wherein each said liposome contains an 8-quinoquinoline selected from the group consisting of primaquine and a pharmaceutically-acceptable acid addition salt thereof.

34. The method of claim 33 wherein the glycoconjugate is selected from the group consisting of:
(a) a glycolipid having a terminal carbohydrate moiety selected from the group consisting of glucosyl, galactosyl and lactosyl;
(b) a glycolipid having a terminal carbohydrate moiety selected from the group consisting of glucosyl, galactosyl and lactosyl encapsulated within a liposome selected from the group consisting of a phospholipid and cholesterol-containing liposome, and a phospholipid, cholesterol and a charged (lipophilic) amphipathic compound-containing liposome; and
(c) a glycolipid having a terminal carbohydrate moiety selected from the group consisting of glycosyl, galactosyl and lactosyl encapsulated within a liposome selected from the group consisting of a phospholipid and cholesterol-containing liposome, and a phospholipid, cholesterol and a charged (lipophilic) amphipathic compound containing liposome wherein each said liposome contains an 8-aminoquinoline selected 35. The method of claim 34 wherein the glycoconjugate is a glycolipid having a terminal carbohydrate moiety selected from the group consisting of glucosyl, galactosyl and lactosyl.

36. The method of claim 34 wherein the glycoconjugate is a glycolipid having a terminal carbohydrate moiety selected from the group consisting of glucosyl, galactosyl and lactosyl encapsulated within a liposome selected from the group consisting of phospholipid and cholesterol-containing liposome, and a phospholipid, cholesterol and a charged (lipophilic) amphipathic compound-containing liposome.

37. The method of claim 34 wherein the glycoconjugate is a glycolipid which contains a terminal carbohydrate moiety selected from the group consisting of glucosyl, galactosyl and lactosyl encapsulated within a liposome selected from the group consisting of a phospholipid and cholesterol-containing liposome, and a phospholipid, cholesterol and a charged (lipophilic) amphipathic compound-containing liposome wherein each said liposome contains an 8-aminoquinoline selected from the group consisting of primaquine and a pharmaceutically-acceptable acid addition salt thereof.

38. The method of claim 35 wherein the glycolipid is ceramide.

39. The method of claim 36 wherein the glycolipid is ceramide.

40. The method of claim 37 wherein the glycolipid is ceramide.

41. The method of claim 38 wherein the carbohydrate moiety is glucosyl.

42. The method of claim 38 wherein the carbohydrate moiety is galactosyl.

43. The method of claim 38 wherein the carbohydrate moiety is lactosyl.

44. The method of claim 39 wherein the carbohydrate moiety is glucosyl.

45. The method of claim 39 wherein the carbohydrate is galactosyl.

46. The method of claim 39 wherein the carbohydrate is lactosyl.

47. The method of claim 40 wherein the carbohydrate is glucosyl.

48. The method of claim 40 wherein the carbohydrate is galactosyl.

49. The method of claim 40 wherein the carbohydrate is lactosyl.

50. The method of claim 48 wherein the liposome contains a phospholipid, cholesterol and a charged (lipophilic) amphipathic compound.

51. The method of claim 50 wherein the phospholip is beta, gamma-dipalmitoylphosphatidylcholine and the charged (lipophilic) amphipathic compound is diacetyl phosphate.

52. The method of claim 51 wherein the 8-aminoquinoline is primaquine diphosphate.

53. The method of claim 33 wherein the glycoconjugate is selected from the group consisting of:
(a) a glycoprotein selected from the group consisting of fetuin, asialofetuin, orosomucoid and asialoorosomucoid encapsulated within a liposome selected from the group consisting of a phospholipid and cholesterol-containing liposome, and a phospholipid, cholesterol and a charged (lipophilic) amphipathic compound-containing liposome; and (b) a glycoprotein selected from the group consisting of a phospholipid and cholesterol-containing liposome, and a phospholipid, cholesterol and a charged (lipophilic) amphipathic compound-containing liposome wherein each said liposome contains an 8-aminoquinoline selected from the group consisting of primaquine and a pharmaceutically-acceptable acid addition salt thereof.

54. The method of claim 53 wherein the glycoconjugate is a glycoprotein selected from the group consisting of fetuin, asialofetuin, orosomucoid and asialoorosomucoid encapsulated within a liposome selected from the group consisting of a phospholipid and cholesterol-containing liposome, and a phospholipid, cholesterol and a charged (lipophilic) amphipathic compound-containing liposome.

55. The method of claim 53 wherein the glyconconjugate is a glycoprotein selected from the group consisting of fetuin, asialofetuin, orosomucoid and asialoorosomucoid encapsulated within a liposome selected from the group consisting of a phospholipid and cholesterol-containing liposome, and a phospholipid, cholesterol and a charged (lipophilic) amphipathic compound-containing liposome wherein each said liposome contains an 8-aminoquinoline selected from the group consisting of primaquine and a pharmaceutically-acceptable acid addition salt thereof.

56. The method of claim 33 wherein the liposome is selected from the group consisting of a phospholipid and cholesterol-containing liposome, and a phospholipid, cholesterol and a charged (lipophilic) amphipathic compound-containing liposome.

57. The method of claim 56 wherein the liposome contains a phospholipid and cholesterol.

58. The method of claim 56 wherein the liposome contains a phospholipid, cholesterol and the additional charged lipid is a (lipophilic) amphipathic compound.

59. The method of claim 57 wherein the phospholipid is selected from the group consisting of a phosphatidylcholine derivative, glycerophosphatide, a lysophosphatide, spingamyelin and mixtures thereof.

60. The method of claim 58 wherein the phospholipid is selected from the group consisting of a phosphatidyl choline derivative, glycerophosphatide, a lysophosphatide, spingomyelin and mixtures thereof.

61. The method of claim 58 wherein the charged amphipathic lipid compound is negatively charged.

62. The method of claim 58 wherein the charged amphipathic lipid compound is positively charged.

63. The method of claim 61 wherein the charged amphipathic lipid compound is selected from the group comprising a di(alkyl) phosphate, a phospholipid, phosphatidic acid, phosphatidylserine, and phosphatidylinositol.

64. The method of claim 62 wherein the charged amphipathic lipid compound is selected from the group comprising long-chain alkylamines, stearylamine, and hexadecylamine.

* * * * *